United States Patent [19]

Ueno

[11] Patent Number: 4,932,867

[45] Date of Patent: Jun. 12, 1990

[54] DEVICE AND PROCESS FOR DETERMINING JAWS POSITION

[75] Inventor: Masato Ueno, Hiroshima, Japan

[73] Assignee: Chugoku Shiken Kabushiki Kaisha, Hiroshima, Japan

[21] Appl. No.: 300,887

[22] Filed: Jan. 24, 1989

[30] Foreign Application Priority Data

Jan. 25, 1988 [JP] Japan .................................. 63-14820

[51] Int. Cl.⁵ ............................................. A61C 19/04
[52] U.S. Cl. ......................................... 433/69; 433/68
[58] Field of Search ...................... 433/72, 75, 68, 69, 433/44, 215; 128/776, 777; 33/513, 514

[56] References Cited

U.S. PATENT DOCUMENTS 2,587,528  2/1952  Robinson .............................. 433/69
2,937,443  5/1960  Skinner .................................. 433/72
3,153,282  10/1964  Brewer .................................. 433/68

FOREIGN PATENT DOCUMENTS 1026797  7/1983  U.S.S.R. ................................ 433/69

Primary Examiner—John J. Wilson
Attorney, Agent, or Firm—Armstrong, Nikaido, Marmelstein, Kubovcik & Murray

[57] ABSTRACT

A device for determining optimum jaws position when full denture is prepared, comprising a height adjustable means to be inserted between upper and lower jaws and a means for detecting and indicating biting pressure applied on the height adjustable means. User of the device, e.g. a denter, can precisely determine the optimum jaws position by detecting a position where the maximum biting pressure is obtained by means of the device.

8 Claims, 5 Drawing Sheets

DEVICE AND PROCESS FOR DETERMINING JAWS POSITION

BACKGROUND OF INVENTION

The present invention relates to a device and a process for determining the jaw position when preparing a full denture, i.e. a set of upper and lower dentures, or one of upper and lower full dentures.

When a full denture is prepared, because the original occlusion before the extraction of teeth cannot be accurately known, it is very difficult to reproduce the optimum upper and lower jaw positions including the motion of muscles supporting the jaws. Therefore, in a conventional process, the jaw position is determined only on the basis of the dentist's experience.

More specifically, in the conventional process, the dentist makes base plates which correspond to the upper and lower jaws of the patient, he mounds wax on both base plates to form wax occlusion rims, and sets those base plates to the patient's mouth.

Then, the dentist gets the patient to repeat biting motions. By adjusting the height of the wax occlusion rims while observing the chewing or biting motion of the patient and his reaction, the dentist determines a jaws position which seems to be optimum.

The above-mentioned conventional process has disadvantages in that it is difficult to obtain an ideal jaw position since the determination is only entrusted to the dentist's judgement and that considerable experience is required of the dentist to find an exact jaw position. Then, in practice, in many cases, the ideal jaw position (i.e. original jaw position before extraction of teeth) cannot be accurately reproduced, and thus the patient cannot experience comfortable chewing and biting motion again.

The object of the present invention is to overcome the above-mentioned problem, and to provide a device and process capable of reproducing the optimum jaw position. Particularly, it has been noticed that the ideal jaw position provides the maximum biting pressure. Therefore, a device and a process capable of determining the ideal jaw position can be realized based on observing the maximum value of the pressure.

SUMMARY OF THE INVENTION

The present invention provides a device for determining the optimum jaw position when a full set of dentures is prepared comprising a height adjustable means to be inserted between a wax occlusion rim put on one of the alveolar ridge surfaces and a base plate put on another alveolar ridge surface to adjust intermaxillary distance, and a means for detecting and indicating the biting pressure applied on the height adjustable means.

The present invention further provides a process for determining the jaw position comprising the step of putting a wax occlusion rim on a surface of one jaw in the patient's mouth, putting a base plate on a surface of another jaw and temporarily bonding a height adjustable means on the base plate by means of a clay-like temporary bonding agent, abutting and setting an end of the height adjustable means with the wax occlusion rim, removing the base plate and the height adjustable means temporarily bonded on the base plate from patient's mouth and fixing the base plate and the height adjustable means with each other by pouring melted wax, setting the fixed base plate and the height adjustable means in the patient's mouth again measuring biting pressure while gradually escalating or reducing the intermaxillary distance by means of the height adjustable means, and fixing the height adjustable means at the height where the maximum pressure is obtained.

The method is carried out as mentioned hereinafter.

The height adjustable means is inserted between the wax occlusion rim and a base plate put the respective upper or lower jaw in the patient's mouth. Next, the height of the height adjustable means is adjusted in low occlusion, i.e. in a state where the intermaxillary distance is small. Then, while gradually escalating or reducing the distance, biting pressure is measured during repetition of the patient's chewing motions. The position where the biting pressure becomes maximum provides the optimum intermaxillary distance, namely the optimum jaw position. A full denture is prepared on the basis of the determined distance.

DETAILED DESCRIPTION

Figure 1:
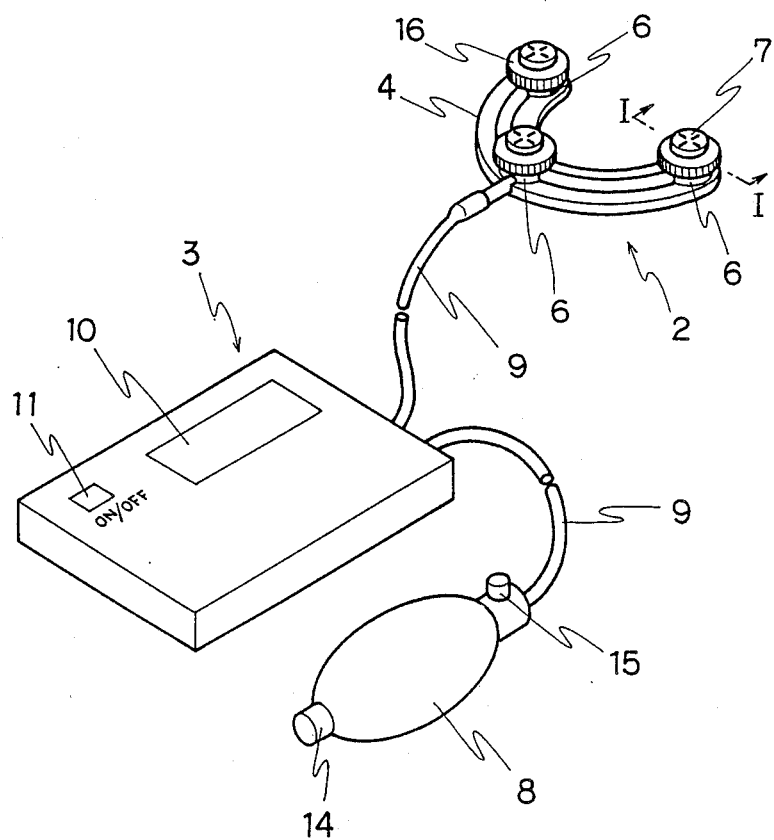
FIG. 1 is a perspective view showing the first embodiment of the device of the present invention.
Figure 2:
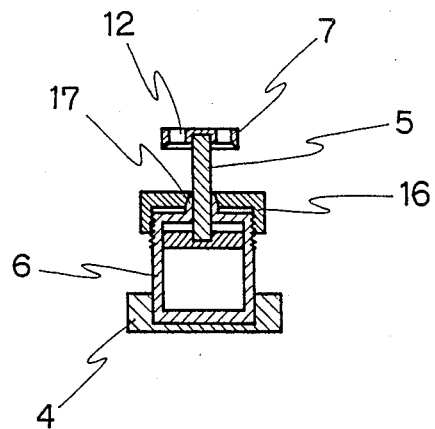
FIG. 2 is a sectional view obtained along lines I—I in FIG. 1.

The first embodiment:

Referring to FIG. 1 and FIG. 2, the numeral 1 denotes a device for determining the jaw position. The device 1 comprises a height adjustable means 2 for adjusting distance between the upper jaw and the lower jaw and a biting pressure display means 3 for detecting and indicating the biting pressure applied on the height adjustable means 2.

The height adjustable means 2 comprises a plate 4 made of synthesized resin with a shape of a dental arch, three sets of pistons 5 and cylinders 6 mounted on the plate 4 at three positions corresponding to the patient's left and right first molar teeth and the median line, disk-like contacting plates 7 abutted against a wax occlusion rim and, a means for actuating the pistion by injecting and exhausting a fluid (e.g. air) to the cylinder 6 (for example, a spheroidal pump or rubber tube 8.)

Compressed air exhausted from the rubber tube 8 is entered into the display means 3 through an air pipe 9. Air pressure due to the biting pressure mentioned after is detected in the display means 3 and the value is displayed on a window 10. The numeral 11 denotes a power switch of the display means 3.

The injected air is further entered into the three cylinders 6 through the air pipes 9. As a piston actuating means, electric compressor can be employed.

The contacting plate 7 is provided with a plurality of slits 12 which have a function to ensure the fixing of wax when the contacting plate is attached to the wax occlusion rim 13 (see FIG. 3) by means of wax.

The rubber tube 8 has an air intake 14 and an exhaust button 15. When the rubber tube 8 is collapsed with a hand, air is delivered toward the cylinder 6 and the piston 5 is pressed out to a height corresponding to the volume of the injected air. When the exhaust button 15 is depressed, the air in the cylinder 6 can be exhausted and the piston 6 can enter into the cylinder 6. The numeral 16 denotes a lock screw for locking the position of the piston 5 and is screwed on the outer surface of the cylinder 6 as shown in FIG. 2. By screwing the lock screw 16 toward the cylinder 6 side, the piston 5 is clamped by clamping pieces 17 provided with the cylinder 6 and is fixed in a desired position.

Figure 3:
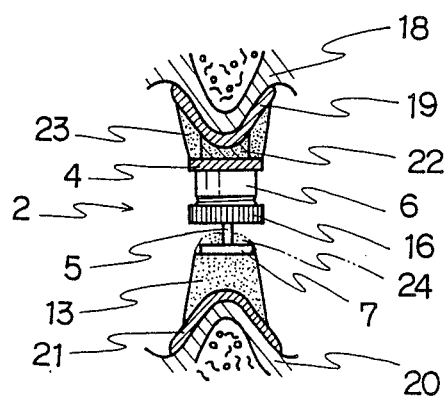
FIG. 3 is a sectional view illustrating the method to operate the device of FIG. 1.

Referring to FIG. 3, use of the above-mentioned device is explained.

First, a base plate 19 is put on the upper jaw 18 in the patient's mouth, and a wax occlusion rim 13 is put on the lower jaw 20. The wax occlusion rim 13 is a wax mounded up on another base plate 21 and flattened at its top surface. A plate 4 of the height adjustable means 2 is then temporarily bonded to the base plate 19 by means of a temporary bonding agent 22 (e.g. resin-clay). Position of the plate 4 is adjusted so that each center of the cylinders 6 and contacting plates of the pistons 5 are situated on three positions (i.e. the left and right first molar teeth and the median line on the crest of the ridge and the wax occlusion rim 13). Thereafter, the patient begins masticating motion after the height adjustable means 2 is turned to an "exhaust" state. During this time, the patient bites so strongly that the occlusion reaches the lowest level. By the strong biting, the temporary bonding agent 22 is crushed, and the plate 4 is temporarily bonded to the base plate 19.

Thereafter, the base plate 19 and the height adjustable means 2 temporarily bonded thereon are taken out of the patient's mouth. The base plate 19 and the height adjustable means 2 are securely fixed by pouring melted wax 23 in a space between the base plate 19 and the plate 4 where temporary bonding agent 22 is absent so as to make an upper wax occlusion rim.

Then, the base plate 19 and the height adjustable means 2 are inserted in the patient's mouth again and are set on the upper jaw 18. Thereafter, by depressing the rubber tube 8, a little volume of air is inserted into the cylinder 6 to project the piston 5. Then, the contacting plate 7 is abutted against the wax occlusion rim 13 to slightly enlarge the intermaxillary distance.

While gradually escalating little by little the intermaxillary distance, the dentist gets the patient to make a masticating motion, and the biting pressure is detected every time by the display means 3. Such steps are repeated until the position where the maximum biting pressure is obtained is determined. After the maximum pressure is found, the lock screw 16 is turned to lock the piston 5 and to maintain the intermaxillary distance to a fixed value. In such a locked state, the patient releases the biting force, and the dentist confirms that a gap between the contacting plate 7 and the surface of the wax occlusion rim 13 is about 2 to 3 mm. By existence of the gap, it is confirmed that the position is the centric occlusion. The centric occlusion means a stable state where opposing cusps and slopes (of artifical teeth) of the upper and lower jaws are in contact with each other with maximum contacting area and the cusps and slopes closely fit with each other, when a full denture or dentures are set in the patient's mouth.

Then, melted wax 24 is poured on the contacting plate 7 to fix the contacting plate 7 to the wax occlusion rim 13.

After that, the upper and lower base plates 19, 21, the wax occlusion rim 13 and the height adjustable means 2 which are fixed with each other are set to an articulator, and a set of full dentures is prepared according to a conventional process.

In the above-mentioned example process, the centric occlusion is determined while escalating the intermaxillary distance. However, in contrast with this, the measurement can be started from the highest state where the jaws are sufficiently opened, and can be carried out while reducing the intermaxillary distance by gradually exhausting the air in order to find the centric occlusion.

The second embodiment:

Since patients' jaws are in various sizes, in case that the dental-arch-shaped plate has a fixed size, there are cases where the sets of pistons and cylinder cannot be precisely arranged on the first molar teeth and the median line. The second embodiment is to eliminate such a problem.

Figure 4:
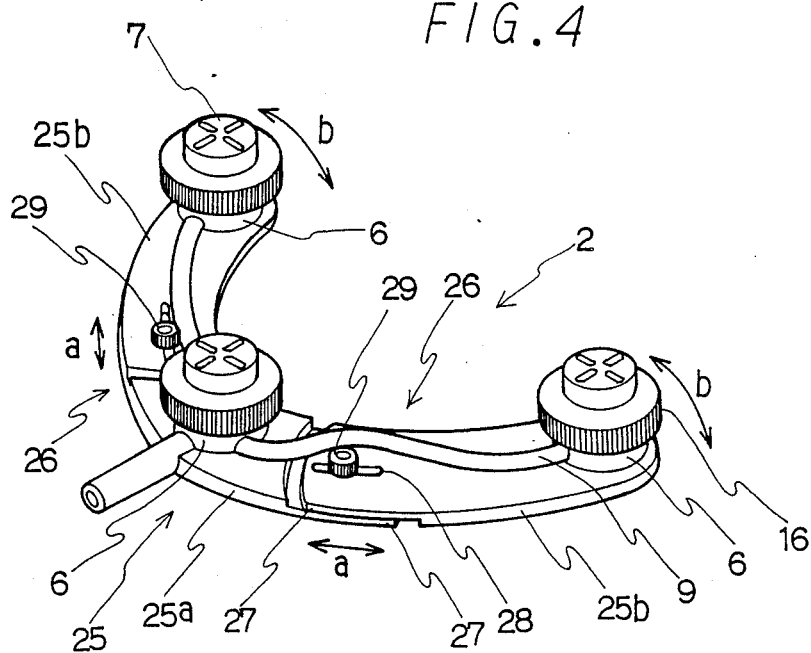
FIG. 4 is a perspective view showing the second embodiment of the device of the present invention.

In the device of the second embodiment, as shown in FIG. 4, the plate 25 has two joints 26 at middle positions which are symmetrical with respect to the median line so that the length of the plate 25 itself is adjustable by expanding and contracting in the directions of arrows a and the distance between both ends of the plate 25 is adjustable by rotating the plates 25 in the directions of arrows b. That is, the plate 25 is separated into three pieces, i.e. center section 25a and left and right sections 25b, 25b.

Those separated sections have thin portions 27 each having elongated hole 28 and the thin portions 27 are piled up and jointed by screws 29 inserted through the elongated holes 28 to form joints 26. When the screws 29 are released, the joints 26 becomes rotatable and extendable. When the screws 29 are tightened, the joints 26 are fixed.

The numeral 9 denotes air pipes for supplying air to the cylinders 6. The air pipes 9 have flexible construction and margin in length in order to enable the expansion and retraction and the rotation of the plates 25b.

According to the above-mentioned construction, the height adjustable means 2 can be precisely positioned on the crest of the patient's ridge, and therefore allowing a better denture to be prepared.

Figure 5:
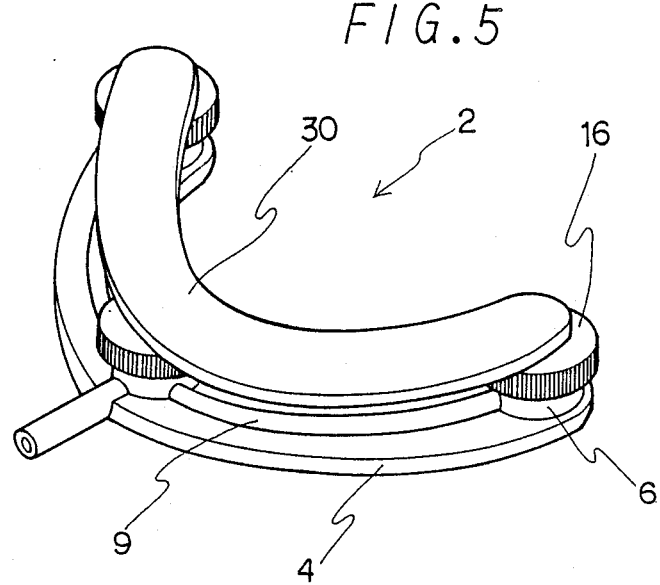
FIG. 5 is a perspective view showing the third embodiment of the device of the present invention.

The third embodiment:

In the device of the third embodiment, the wax occlusion rim contacting plate 30 is an integral plate having a shape of a dental arch as is shown in FIG. 5. In this construction, though the distance between the plate 4 and the contacting plate 30 is fixed, there is no problem since the difference between the upper and lower jaws can be absorbed by the temporary bonding agent 22 (see FIG. 3) such as cray.

Further, in the device of the third embodiment, the same mechanism of plate 25 as mentioned in the second embodiment can be employed in the plate 30 to make the plate 30 adjustable. Another construction in the third embodiment is the same as the above-mentioned embodiments.

The fourth embodiment:

In the device of the fourth embodiment, a liquid (e.g. glycerine) is employed as a fluid to be injected in a cylinder from a piston-actuating-means and to be exhausted from the cylinder.

Figure 6:
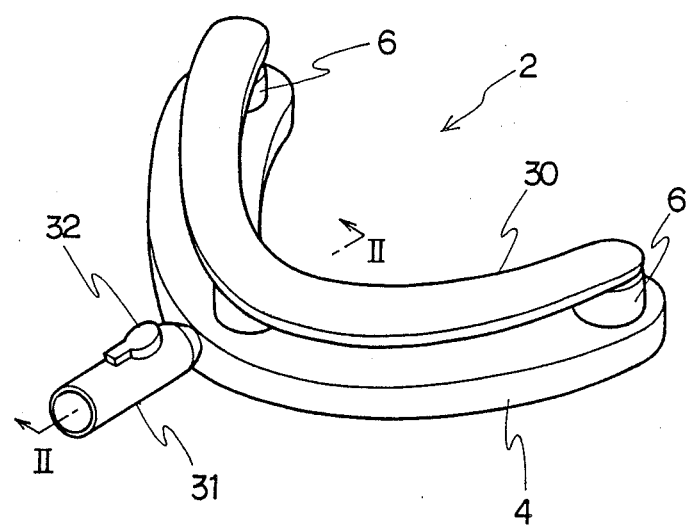
FIG. 6 is a perspective view showing the fourth embodiment of the device of the present invention.
Figure 7:
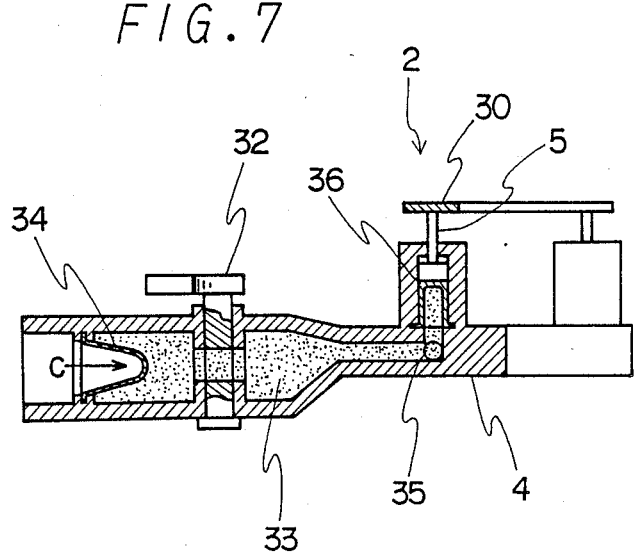
FIG. 7 is a sectional view obtained along lines II—II in FIG. 6.

Referring to FIG. 6 and FIG. 7, the numeral 31 denotes a pipe made of metal or synthesized resin. The end of the pipe 31 is fixed at the front end of a plate 4. The pipe 31 is provided with a cock or valve 32 for enabling or stopping the flow of the liquid 33 by rotating the valve 32.

In FIG. 7, the valve 32 is turned to an open position for enabling the flow of liquid. The numeral 34 denotes a diaphragm made of a rubber-like elastomeric material, (e.g. nitrile rubber). The diaphragm 34 is provided in the pipe 31 at a position adjacent the valve 32.

Therefore, when the valve 32 is turned to the open state and air pressure in the air pipe 9 is raised by collapsing the rubber tube 8 (see FIG. 1), the pressure is applied to the diaphragm 34 as a piston actuating force. Then, the diaphragm 34 is inflated in the right direction as shown by arrow c in FIG. 7 thereby pressing the liquid 33 to raise the piston 5.

In the reverse, when the piston 5 is depressed while pressing the exhaust button 15 (see FIG. 1), the diaphragm 34 moves in the left direction or shrinks.

As mentioned above, the liquid 33 flows in a sealed state in the cylinder 6 and in a passage or pipe 35 communicating to the cylinder 6. The pipe 35 is formed in the plate 4 and communicates with the three cylinders 6.

In the above-mentioned structure, another elastomeric membrane 36 made of, for example, nitrile rubber can be arranged in the cylinder 6 in order to prevent leaking of the liquid 33.

When liquid 33 employed as a fluid, as is in the present embodiment, any lock screw 16 (see FIG. 1) or the like which is used in the preceding embodiments is not necessary, since change of volume due to compression is very small in liquid. That is to say, a gas fluid is slightly compressable, but a liquid is substantially uncompressable.

In the device of the present (the fourth) embodiment, at a position of the piston 5 where biting pressure is maximum, if the valve 32 is turned to close and the flow of the liquid is stopped, the motion of the piston is locked. Further, when a plate is used for contacting plate 30, each piston is also locked.

Figure 8:
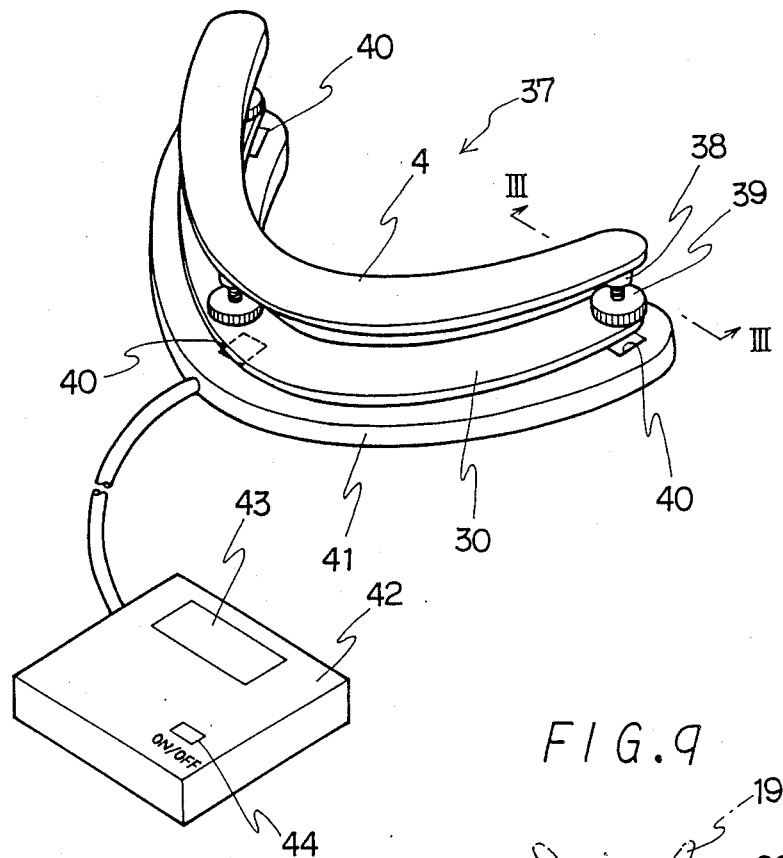
FIG. 8 is a perspective view showing the fifth embodiment of the device of the present invention.
Figure 9:
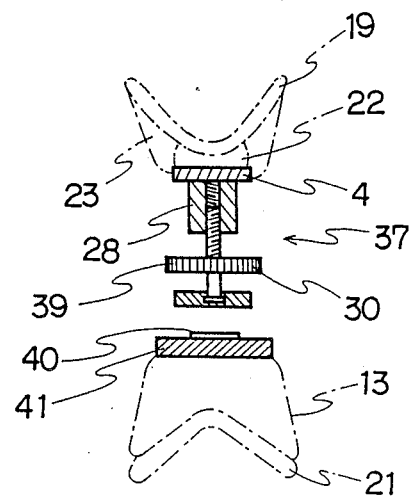
FIG. 9 is a sectional view obtained lines III—III in FIG. 8.

The fifth embodiment:

Referring to FIG. 8 and FIG. 9, the height adjustable means 37 comprises a plate 4 having a form dental arch form, three nut members 38 fixed on the plate 4 at three positions corresponding to the first molar teeth and the median line, bolt members 39 screwed in the nut members 38 for vertical movement by rotation, a contacting plate 30 connected at the top ends of the bolt members 39, a wax occlusion plate 41 to be put on a wax occlusion 13 and three pressure detectors or pressure sensors 40 arranged on the wax occlusion plate 41 at three positions corresponding to the first molar teeth and the median line. The bolt member 39 is supported on the contacting plate 30 in a rotatable manner.

A biting pressure displaying means 42 receives detected signals from the three pressure sensors and indicates the signals on the display window 43 as digital indications. The numeral 44 denotes a power switch. The numeral 13 denotes a wax occlusion rim, and the numeral 21 denotes a lower jaw base plate.

The above-mentioned device can be operated in the substantially same manner as explained in the prescribed embodiments.

First, the plate portion 4 is temporarily bonded on the base plate 19 through temporary bonding agent 22, the bolt members 39 are rotated by fingers or the like to move (in the drawing) the contacting plates 30 fixed on the top end of the bolt members 39 in an upward direction, and the contacting plates 30 are set at a lower occlusion position by getting the patient to make chewing motion. Then, the height adjustable means and the base plate 19 are taken out of the patient's mouth, are fixed with wax 23, and are set again on the upper jaw in the mouth.

Next, the bolt member 39 is rotated by fingers to move downwardly. While escalating the intermaxillary distance and getting the patient to make chewing motions, the biting pressure is detected.

By repeating the above-mentioned process, the maximum biting pressure is detected and the optimum jaw position is determined.

According to the present invention, by providing a height adjustable means to be inserted between the upper and lower jaws capable of adjusting the intermaxillary distance, and a biting pressure displaying means for detecting and indicating the biting pressure applied on the height adjustable means, the intermaxillary distance where maximum biting pressure is obtained can be easily found.

Further, by confirming that a gap between the contacting plate and the wax occlusion rim is about 2 to 3 mm after the patient releases his biting muscle, the dentist can determine that the obtained position is the centric occlusion. Then the ideal jaw position can be precisely reproduced.

Though several embodiments are described in detail, it is to be understood that the present invention is not limited to the above-mentioned embodiments, and various changes and modifications may be made in the invention without departing from the spirit and scope thereof.

What we claim is:

1. A device for determining optimum jaw position when a full denture is prepared, comprising:
    a wax occlusion rim adapted for being placed on a surface of one of a patient's alveolar ridge;
    a base plate adapted for being placed on a surface of a second of the patient's alveolar ridge;
    height adjustable means for adjusting a gap between said occlusion rim and said base plate and adapted for being inserted between said occlusion rim and said base plate,
    said height adjustable means having a first plate with a dental arch shape, three pairs of a piston and a cylinder each pair arranged on the plate at one of three positions corresponding to positions of left and right first molar teeth and to a mid-point on the first plate along the dental arch shape, a wax-occlusion-rim-contacting plate positioned on top of the pistons, and piston-actuating-means for supplying a fluid in the cylinders and for exhausting the fluid from the cylinders to move the pistons,
    each cylinder having locking means to lock into position each piston; and
    means for detecting and indicating biting pressure applied on said height adjustable means.

2. A device as set forth in claim 1 wherein, said wax-occlusion-rim-contacting plate is a plate having a dental arch shape and is jointed to each of the three pistons.

3. A device as set forth in claim 1 wherein, said fluid to be supplied in and exhausted from the cylinder is gas.

4. A device as set forth in claim 1 wherein, said first plate having the dental arch shape further comprises:
   a center section;
   a right section;
   a left section, and
   adjustable joint means for jointing said center section to each of said right and left sections such that said right and left sections can rotatably and extendably move relative to said center section and thereby vary the dental arch shape, and the positions of the pistons and cylinders relative to each other.

5. A device for determining optimum jaw position when a full denture is prepared, comprising:
   a wax occlusion rim adapted for being placed on a surface of one of a patient's alveolar ridge;
   a base plate adapted for being placed on a surface of a second of the patient's alveolar ridge;
   height adjustable means for adjusting a gap between said occlusion rim and said base plate and adapted for being inserted between said occlusion rim and said base plate,
   said height adjustable means having a first plate with a dental arch shape, three pairs of a piston and a cylinder each pair arranged on the plate at one of three positions corresponding to left and right first molar teeth and to a mid-point on the first plate along the dental and shape, pipes for communicating liquid between the cylinders, a wax-occlusion-rim-contacting plate positioned on top of the pistons, and piston-actuating-means for supplying a liquid in the cylinders and for exhausting the liquid from the cylinders to move the pistons wherein the piston-actuating-means uses a diaphragm made of rubber-like elastomeric material to produce an actuating force and the liquid is sealed in the cylinders and the pipes; and
   means for detecting and indicating biting pressure applied on said height adjustable means.

6. A device as set forth in claim 5 wherein an amount of the liquid in the cylinders is fixed by a valve provided connected to the diaphragm.

7. A device for determining optimum jaw position when a full denture is prepared, comprising:
   a wax occlusion rim adapted for being placed on a surface of one of a patient's alveolar ridge;
   a base plate adapted for being placed on a surface of a second of the patient's alveolar ridge;
   height adjustable means for adjusting a gap between said occlusion rim and said base plate and adapted for being inserted between said occlusion rim and said base plate,
   said height adjustable means having a first plate with a dental arch shape, nut members fixed on the plate at three positions corresponding to position of left and right first molar teeth and to a mid-point on the first plate along the dental arch shape, bolt members screwed in the nut members for vertical movement by rotation thereof, contacting plates connected to each said bolt member, a wax occlusion rim plate adapted to be placed on said wax occlusion rim, and pressure sensors arranged on the wax occlusion rim plate corresponding to the left and right first molar teeth positions and to the mid-point on the first plate with a dental arch shape, said pressure sensors adapted for detecting biting pressure applied through the contacting plates; and
   displaying means for displaying biting pressure that is detected.

8. A process for determining optimum jaws position of a patient comprising the steps of:
   (a) putting a wax occlusion rim on one jaw surface, putting a base plate on another jaw surface, and temporarily bonding a height adjustable means on the base plate using a temporary bonding agent;
   (b) abutting a top end of the height adjustable means against the wax occlusion rim and setting the height adjustable means in a low or high occlusion;
   (c) taking out the height adjustable means in a temporarily bonded state, and fixing the base plate and height adjustable means by pouring melted wax therebetween;
   (d) setting the base plate and the height adjustable means again in the patient's mouth, and measuring biting pressure while escalating or reducing intermaxillary distance by means of the height adjustable means; and
   (e) fixing the height adjustable means at a position where maximum biting pressure is obtained.

* * * * *